United States Patent
Binder

(10) Patent No.: US 10,420,621 B1
(45) Date of Patent: Sep. 24, 2019

(54) GLOVE REMOVER

(71) Applicant: Kurwin J. Binder, Pembroke, MA (US)

(72) Inventor: Kurwin J. Binder, Pembroke, MA (US)

( * ) Notice: Subject to any disclaimer, the term of this patent is extended or adjusted under 35 U.S.C. 154(b) by 105 days.

(21) Appl. No.: 15/787,013

(22) Filed: Oct. 18, 2017

Related U.S. Application Data

(60) Provisional application No. 62/409,418, filed on Oct. 18, 2016.

(51) Int. Cl.
*A61B 42/50* (2016.01)
*A61B 42/40* (2016.01)

(52) U.S. Cl.
CPC .............. *A61B 42/50* (2016.02); *A61B 42/40* (2016.02)

(58) Field of Classification Search
CPC ...... A47G 25/90; A47G 25/904; A47G 25/92; A61B 42/50
See application file for complete search history.

(56) References Cited

U.S. PATENT DOCUMENTS

| | | | |
|---|---|---|---|
| 2,741,410 A | 4/1956 | Violette | |
| 3,695,493 A | 10/1972 | Karr | |
| 4,876,747 A | 10/1989 | Coffey et al. | |
| 4,915,272 A | 4/1990 | Vlock | |
| 5,058,785 A | 10/1991 | Rich et al. | |
| 5,078,308 A * | 1/1992 | Sullivan | A47G 25/904 |
| | | | 206/278 |
| 6,021,935 A | 2/2000 | Yonezawa | |
| 6,053,380 A | 4/2000 | Sherrod | |
| 6,193,117 B1 * | 2/2001 | Poschelk | A61B 42/50 |
| | | | 223/111 |
| D440,740 S * | 4/2001 | Anctil | D2/641 |
| 6,241,134 B1 | 6/2001 | Dunkel | |
| 6,279,792 B1 | 8/2001 | Neal | |
| 6,419,131 B1 * | 7/2002 | Rix | A47G 25/904 |
| | | | 223/111 |
| 6,427,883 B1 | 8/2002 | Eaten | |
| 6,435,388 B1 | 8/2002 | Binder et al. | |
| 6,554,168 B2 | 4/2003 | Stobart | |
| 6,834,784 B1 | 12/2004 | Webber et al. | |
| 7,712,642 B2 | 5/2010 | Gaines et al. | |
| 7,726,526 B2 | 6/2010 | Cattenhead | |
| 8,220,675 B2 | 7/2012 | Rohard | |
| 8,695,118 B2 | 4/2014 | Schrodl | |
| 10,034,566 B1 * | 7/2018 | Shin | A47G 25/904 |
| 2001/0007329 A1 | 7/2001 | Stobart | |
| 2002/0158092 A1 | 10/2002 | Cattenhead | |
| 2004/0149788 A1 * | 8/2004 | Sato | A47G 25/904 |
| | | | 223/111 |
| 2007/0170213 A1 | 7/2007 | Gaines et al. | |
| 2007/0170214 A1 | 7/2007 | Kelly | |
| 2008/0217366 A1 | 9/2008 | Rohard | |

FOREIGN PATENT DOCUMENTS

FR  2614517 A1 * 11/1988 ........... A47G 25/904

* cited by examiner

*Primary Examiner* — Nathan E Durham
(74) *Attorney, Agent, or Firm* — John P. McGonagle

(57) ABSTRACT

An apparatus for removing and disposing of contaminated gloves is provided. The apparatus has a vertical frame with a hook assembly on top which is operatively connected to a pedal assembly at the frame bottom. A shelf below the hook assembly supports a container for receiving discarded gloves.

4 Claims, 6 Drawing Sheets

GLOVE REMOVER

CROSS-REFERENCE TO RELATED APPLICATIONS

Applicant claims the priority benefits of U.S. Provisional Patent Application No. 62/409,418, filed Oct. 18, 2016.

BACKGROUND OF THE INVENTION

This invention relates to gloves, and in particular, to an apparatus for removing gloves from the hands of a wearer.

Protective gloves are commonly used for activities where it is desired to provide a barrier between the wearer and the material handled by the wearer. Such gloves are typically fabricated from a thin gauge elastomeric material such as latex or natural rubber. Elastomeric gloves stretch to the shape of the hand. Due to the close fit requirements for this class of gloves, it is difficult to remove them while maintaining protective and sanitary integrity.

It is desirable to have an apparatus that will aid a wearer in the safe removal of elastomeric gloves without the assistance of the wearer's opposite hand or another person.

SUMMARY OF THE INVENTION

The present invention addresses this need by providing an apparatus which removes and disposes of a contaminated glove in one step without risking cross-contamination between the exterior surface of the glove and the wearer or other personnel.

These together with other objects of the invention, along with various features of novelty which characterize the invention, are pointed out with particularity in the following detailed description and claims. For a better understanding of the invention, its operating advantages and the specific objects attained by its uses, reference should be made to the accompanying drawings and descriptive matter in which there is illustrated a preferred embodiment of the invention.

DETAILED DESCRIPTION OF THE INVENTION

Figure 1:
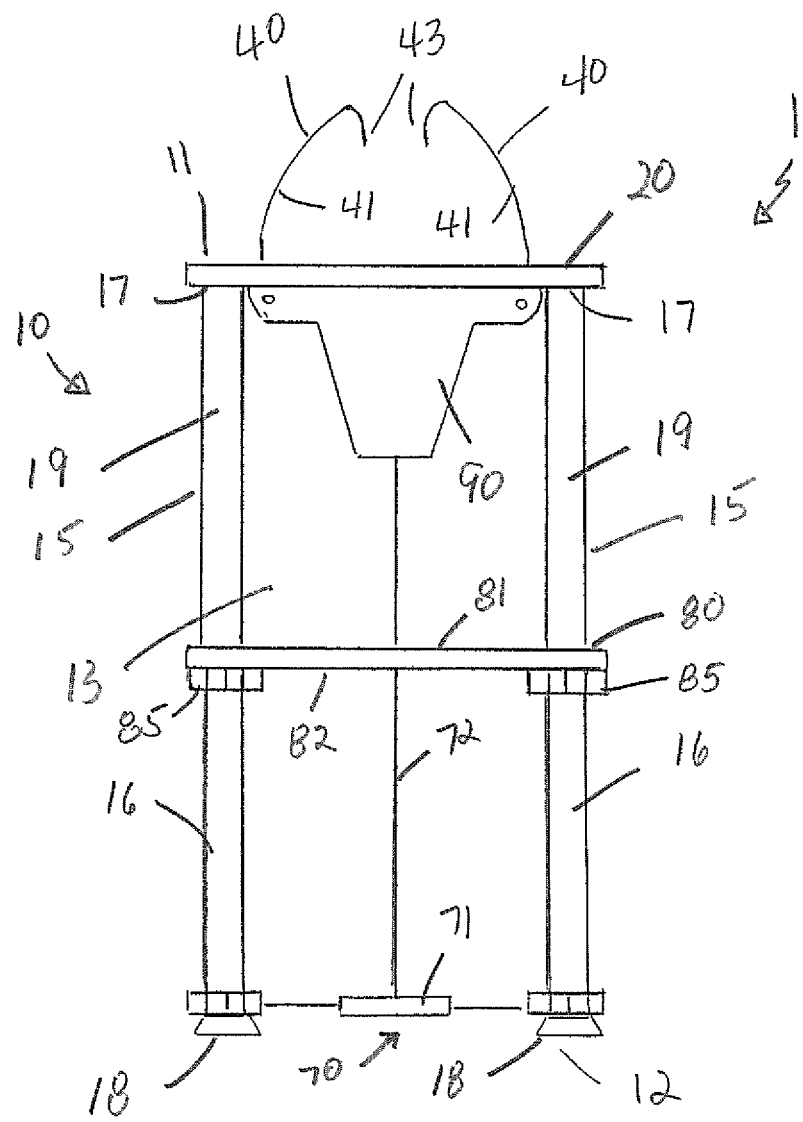
FIG. 1 is a front view of the glove remover.
Figure 2:
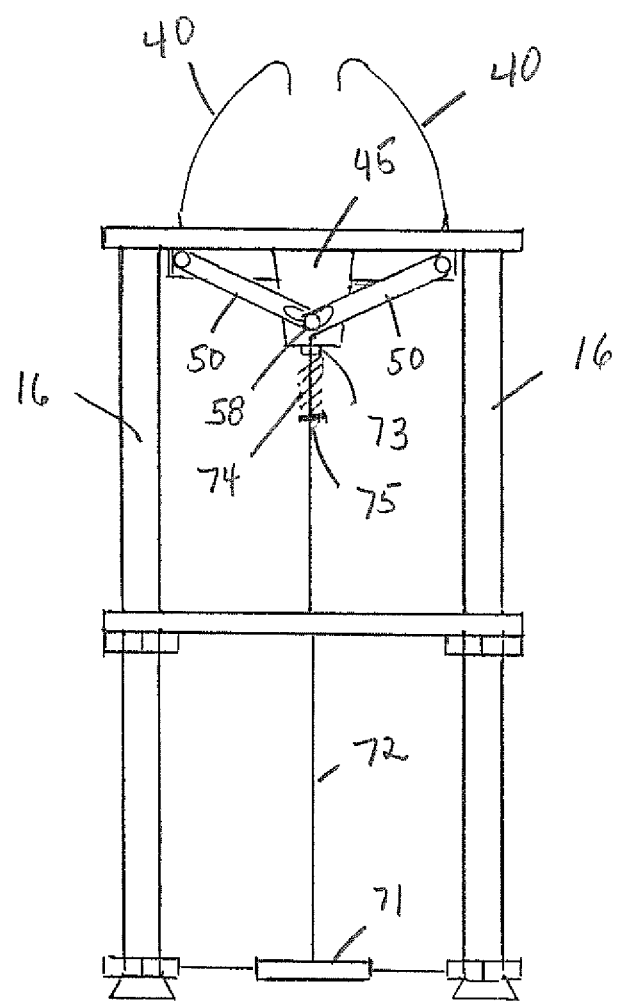
FIG. 2 is a front view of the glove remover without the protective shield.
Figure 3:
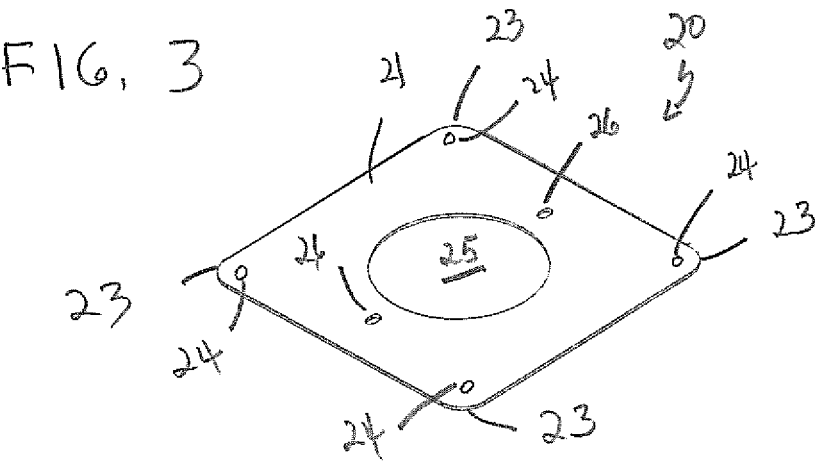
FIG. 3 is a top perspective view of the top plate.
Figure 4:
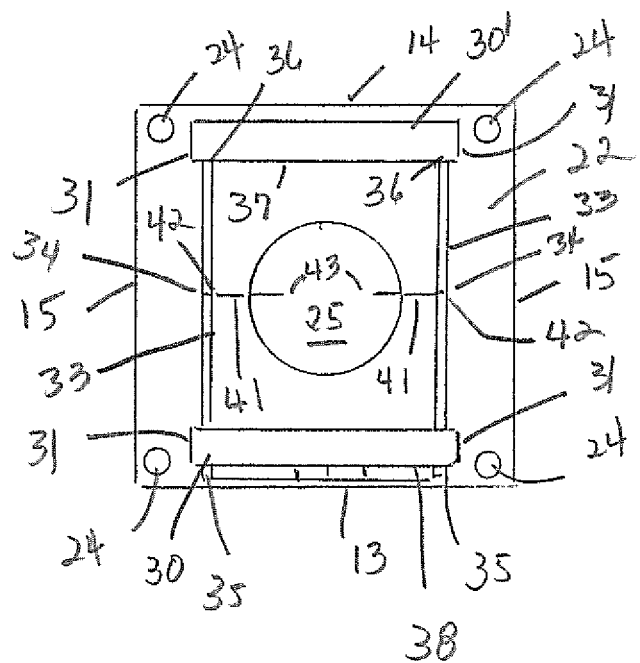
FIG. 4 is a bottom view of the top plate.
Figure 5:
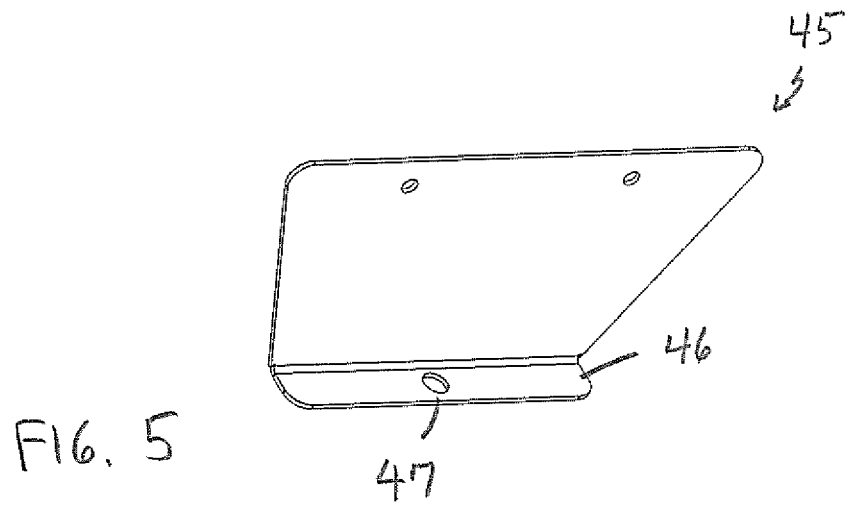
FIG. 5 is a front perspective view of the brace bracket.
Figure 6:
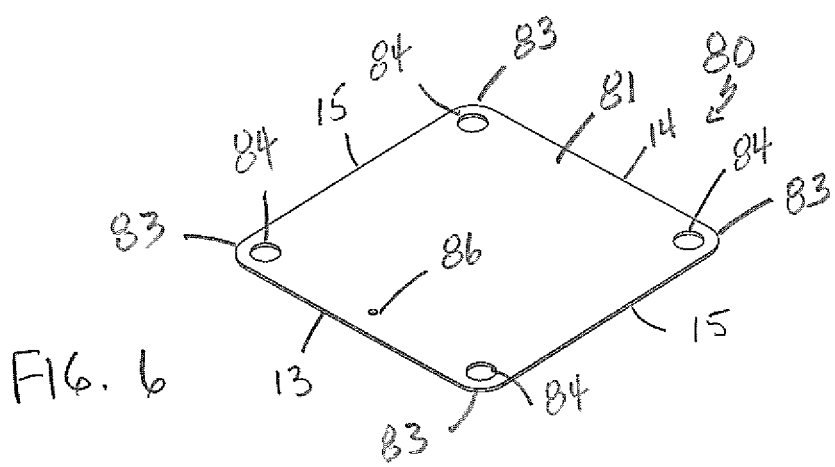
FIG. 6 is a top perspective view of the shelf.
Figure 7:
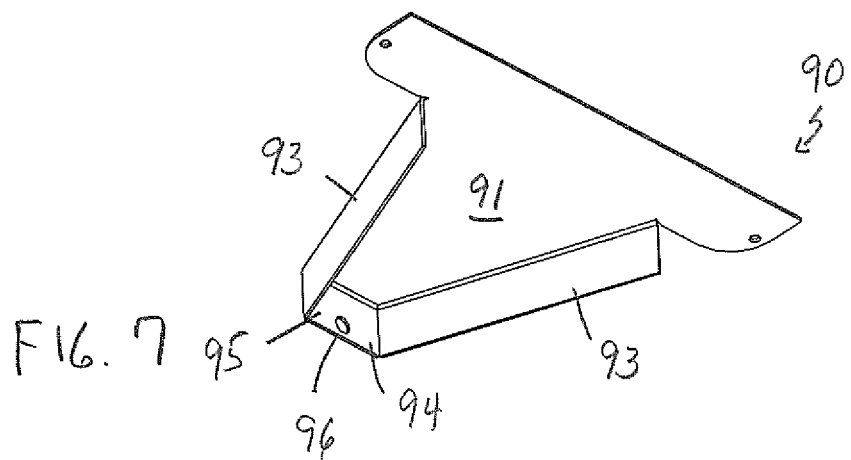
FIG. 7 is a front perspective view of the protective shield.
Figure 8:
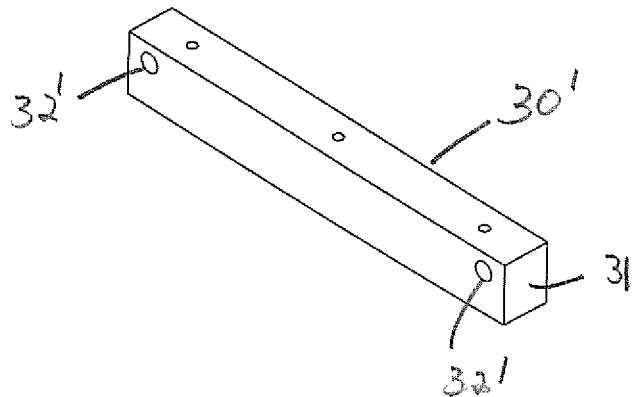
FIG. 8 is a front perspective view of the rear brace.
Figure 9:
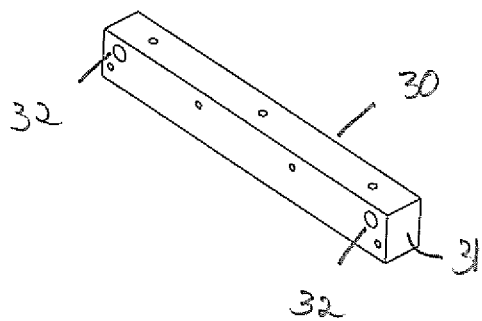
FIG. 9 is a front perspective view of the front brace.
Figure 10:
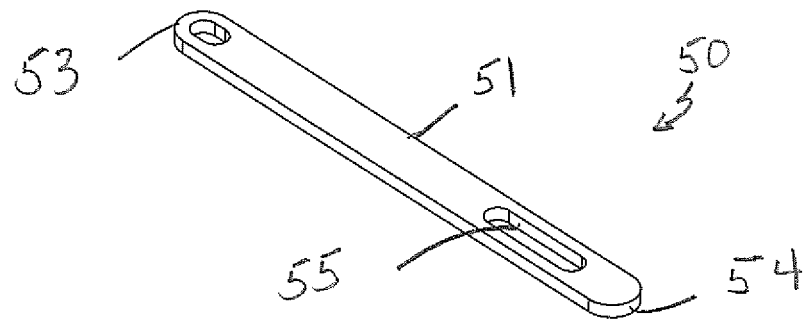
FIG. 10 is a bottom perspective view of an elongated member.
Figure 11:
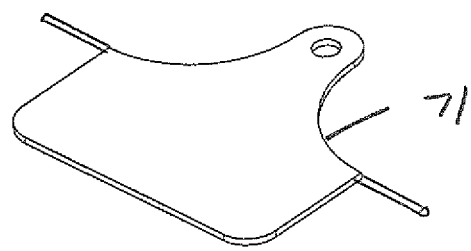
FIG. 11 is a top perspective view of the pedal.
Figure 12:
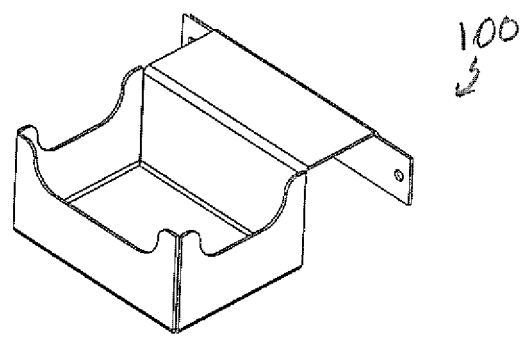
FIG. 12 a top perspective view of the holder.

Referring to the drawings in detail wherein like elements are indicated by like numerals, there is shown a preferred embodiment of a glove remover 1 comprised of a vertical upright frame 10 with a top hook assembly 40 operatively connected to a foot pedal assembly 70.

The frame 10 has a generally rectangular body with a top 11, bottom 12, front 13, rear 14, and two opposite sides 15.

The frame 10 is further defined by four vertical support poles 16, each support pole having a top end 17, a bottom end 18, and an elongated pole body 19 preferably having a circular cross-section. Each support pole is positioned at a junction of the frame front and opposite sides and at a junction of the frame rear and opposite sides.

The frame top 11 is defined by a generally rectangular top plate 20. The top plate 20 has a top surface 21, a bottom surface 22 and four corners 23. The top plate has an aperture 24 adjacent each corner 23. Each support pole top end 17 terminates in a top plate corner aperture 24. The top plate 10 is further comprised of a substantial annular, central aperture 25. The top plate 10 is further comprised of two channel apertures 26, each formed adjacent the central aperture toward a frame side 15.

The top plate bottom surface 22 has two elongated, identical braces 30 attached thereto, one along the frame front 13 and one along the frame rear 14. Each brace 30 has a generally rectangular cross-section and two opposite ends 31 defining a brace longitudinal axis, each said longitudinal axis parallel to the frame front 13 and rear 14. Each brace end 31 terminates adjacent a support pole body 19. The front brace 30 has two front to back apertures 32 formed therein, each said aperture adjacent a brace end 31. The rear brace 30' has two apertures 32' formed into a rear brace front side 37, each said aperture adjacent a brace end. The front brace 30 is further comprised of a downwardly extending bracket 45 attached to a front brace front side 38 terminating in a forwardly extending flange 46. The flange 46 has a central aperture 47 formed therein.

An elongated axle 33 is inserted through each front brace aperture 32, and extending into a corresponding rear brace aperture 32'. Each axle has a front end 35 protruding through a front brace aperture 32 toward the frame front 13. Each axle has a rear end 36 inserted into a rear brace aperture 32'. At an approximate longitudinal mid-point 34 on each axle 33, a hook assembly 40 is fixedly attached, said hook assembly having a body 41 with an axle connection end 42 and a free end 43. Each hook body 41 extends through a top plate channel aperture 26, with the hook free end 43 positioned upward and over a portion of the top plate central aperture 25.

Each axle front end 35 terminates in a flat, elongated member 50 having a front surface 51 and a rear surface 52, an attachment end 53 and a distal end 54, said attachment end and distal end defining a member longitudinal axis. Each elongated member is further comprised of an elongated channel opening 55 near to the member distal end 54, and extending from the front surface through the rear surface. Each member longitudinal axis is positioned nominally 30 degrees downwardly from its attached axle toward a front center. The two members are joined together by means of a pin 58 inserted through each member channel opening 55.

The glove remover is further comprised of a pedal assembly 70 having a pedal 71 pivotally joined to the front support pole bodies 19 near to the support pole bottom ends 18. The pedal 71 is attached to an elongated vertical rod 72 terminating in a top clip 73 attached to said pin 58. The rod 72 passes through the brace bracket flange aperture 47. A spiral spring 74 is placed about the rod, beneath the bracket flange aperture 47. The spiral spring bottom 75 is attached to the rod a desired distance below the brace bracket flange 46.

In operation, an operator foot is pressed against the pedal 71 driving the rod 72 vertically upward compressing the spring 74 against the bracket flange 46. The upward movement of the rod pushes the clip 73 and attached pin 58 upward. This action forces the elongated member distal ends 54 upward. The upward movement of the member distal ends 54 causes the member attachment ends to rotate the attached axles 33 thereby pivoting the hook fee ends 43 up and away from the top plate central aperture 25. This allows an operator to reach a gloved hand down into the central aperture. Gradual release of the pressure on the pedal 71 causes the spring 74 to force the rod 72 downward reversing the movement of the hooks 40 and moving the hook free ends downward and toward the center of the central aperture 25. The operator then pulls his/her hand up as the hook free ends 43 grasp a glove cuff, thereby allowing the operator to have the glove removed from his/her hand without actually touching the glove.

The glove remover is further comprised of a shelf 80 having a top surface 81, a bottom surface 82 and four corners 83. The shelf has an aperture 84 adjacent each corner 83. Each support pole body 19 is slid through a shelf corner aperture 84. A clip 85 is attached to the shelf bottom surface 82 at each aperture 84, thereby holding the shelf in a vertical position to the poles 16. The shelf 80 has a rod aperture 86 formed from the top surface through the bottom surface, adjacent a shelf front, at an approximate midpoint between two of the support poles 16. The vertical rod 72 is slid through the shelf rod aperture. The shelf provides means for stabilizing the structure of the glove remover as well as providing a surface to hold a container beneath the top plate central aperture for discarded gloves.

The glove remover 1 may also be comprised of a protective shield 90 attached to the frame front 13. The shield 90 has front 91, rear 92, two opposite sides 93 and a bottom 94, said bottom terminating in a rearward flange 95. The flange 95 has a central aperture 96 formed therein. The shield 90 is attached to the front brace 30, near to the brace ends 31. The shield flange central aperture 96 fits over the rod 72. The shield 90 protects the top portion of the rod, the rod spring 74, pin 58 and members 50 from any external frontal actions.

A holder 100 may be attached to the top plate 20 or rear brace 30' at the frame rear 14. The holder 100 preferably has a cup-like shape and is adapted to hold containers of unused gloves.

It is understood that the above-described embodiment is merely illustrative of the application. Other embodiments may be readily devised by those skilled in the art which will embody the principles of the invention and fall within the spirit and scope thereof.

I claim:

1. An apparatus for removing and disposing of a contaminated glove in one step without cross-contamination between an exterior surface of the glove and a glove wearer, comprising:
  a vertical upright frame having a rectangular body with a top, bottom, front, rear and two opposite sides, said frame being further defined by four vertical support poles, each support pole having a top end, a bottom end, an an elongated pole body, wherein a support pole is positioned at a junction of the frame front and opposite sides and at a junction of the frame rear and opposite sides, wherein said frame top is defined by a rectangular top plate having a top surface, a bottom surface and four corners, said top plate having an aperture adjacent each corner, wherein each support pole top end terminates in a top plate corner aperture, said top plate further comprised of an annular, central aperture, said top plate also further comprised of two channel apertures each formed adjacent the central aperture toward a frame side, wherein said top plate bottom surface has two elongated, identical braces attached thereto, one along the frame front and one along the frame rear, each said brace having a rectangular cross-section and two opposite ends defining a brace longitudinal axis, each said brace longitudinal axis parallel to the frame front and rear, each said brace end terminating adjacent a support pole body, wherein the front brace has two front to back apertures formed therein, each said front to back aperture adjacent a front brace end, wherein the rear brace has two apertures formed into a rear brace front side, each said rear brace aperture adjacent a rear brace end, wherein said front brace is further comprised of a downwardly extending bracket attached to a front brace front side terminating in a forwardly extending flange, said forwardly extending flange having a central aperture formed therein, wherein an elongated axle is inserted through each front brace aperture and extending into a corresponding rear brace aperture, each said axle having a front end protruding through a front brace aperture toward the frame front, each said axle having a rear end inserted into a rear brace aperture;
  a hook assembly fixedly attached at an approximate longitudinal mid-point on each axle, said hook assembly having two bodies each with an axle connection end and a free end, each hook body extending upward through a top plate channel aperture with the hook free end positioned upward and over a portion of the top plate central aperture;
  wherein, each axle front end terminates in a flat, elongated member having a front surface, a rear surface, an attachment end and a distal end, said attachment end and distal end defining a member longitudinal axis, wherein each said elongated member is further comprised of an elongated channel opening near to the member distal end, and extending from the front surface through the rear surface, each member longitudinal axis being positioned 30 degrees downwardly from its attached axle toward a front center, wherein said members are joined together by means of a pin inserted through each member channel opening; and
  a foot pedal assembly operatively connected to said frame and hook assembly, wherein said foot pedal assembly has a pedal pivotally joined to the front support pole bodies near to the support pole bottom ends, wherein said pedal is attached to an elongated vertical rod terminating in a top clip attached to said pin wherein said vertical rod passes through the brace bracket flange aperture.

2. The apparatus as recited in claim 1, further comprising:
a shelf having a top surface, a bottom surface and four corners, said shelf having an aperture adjacent each corner, wherein each said support pole body is slidably positioned through a shelf corner aperture, wherein a fastener is attached to the shelf bottom surface at each aperture to hold the shelf in a vertical position to the support poles, wherein the shelf has a rod aperture formed from the top surface through the bottom surface, adjacent a shelf front, at an approximate midpoint between two of the support poles, wherein said vertical rod is slid through the shelf rod aperture.

3. The apparatus as recited in claim 2, further comprising:
a protective shield attached to the frame front, said shield having a front, a rear, two opposite sides and a bottom, said bottom terminating in a rearward flange, said rearward flange having a central aperture formed therein, wherein the shield is attached to the front brace, near to the front brace ends, wherein the shield rearward flange central aperture fits over the vertical rod.

4. An apparatus as recited in claim 3, further comprising:
a spiral spring placed about the vertical rod, beneath the bracket flange aperture, wherein a spiral spring bottom is attached to the rod a below the brace bracket flange.

\* \* \* \* \*